United States Patent [19]
Kobayashi

[11] Patent Number: 6,107,503
[45] Date of Patent: Aug. 22, 2000

[54] ASYMMETRIC ZIRCONIUM CATALYST

[75] Inventor: Shu Kobayashi, Tokyo, Japan

[73] Assignee: Japan Science and Technology Corporation, Japan

[21] Appl. No.: 09/038,132

[22] Filed: Mar. 11, 1998

[30] Foreign Application Priority Data

Jul. 23, 1997 [JP] Japan .................................. 9-197589

[51] Int. Cl.$^7$ ............................ C01G 25/00; C01G 25/04

[52] U.S. Cl. ............................................ 556/54; 556/56

[58] Field of Search ........................ 556/54, 56; 560/34, 560/43; 568/74; 549/494; 546/256

[56] References Cited

PUBLICATIONS

Database CAPLUS on STN, Acc. No. 1968:502663, Andra, 'Cyclic Esters of Zirconium and Thorium,' Z. Anorg. Allg. Chem. (1968), 361 (5–6), p. 254–8, abstract, 1968.

*Primary Examiner*—Gary Geist
*Assistant Examiner*—Brian J. Davis
*Attorney, Agent, or Firm*—Wenderoth, Lind & Ponack, L.L.P.

[57] ABSTRACT

It is made possible to carry out asymmetric organic syntheses such as an asymmetric imono aldol reaction etc. catalytically with high reactivity and selectivity. An asymmetric zirconium catalyst having a structure that zirconium (IV) being an active central atom of the catalyst and being bonded via oxygen atoms to two molecules of optically active binaphthyl groups is proposed.

15 Claims, 3 Drawing Sheets

ASYMMETRIC ZIRCONIUM CATALYST

FIELD OF THE INVENTION

The invention of the present application relates to an asymmetric zirconium catalyst and a preparation method thereof in which zirconium modified by an optically active binaphthol is contained as an active center, as well as a preparation method of an optically active compound by using it.

PRIOR ART AND PROBLEM

Hitherto, as one important preparation method of optically active nitrogen-containing compounds, there is known an asymmetric imino aldol reaction, but it is limited to only a diastereoselective reaction with using an optically active reaction substrate (Angew. Chem., Int. Ed. Engl., Vol. 34, page 2861, 1995; J. Org. Chem., Vol. 51, page 6902, 1993; J. Am. Chem. Soc., Vol. 112, page 8215, 1990, etc.) or a method requiring a stoichiometric or more asymmetric origin (Angew. Chem., Int. Ed. Engl., Vol. 35, page 981, 1996; Liebigs Ann. Chem., page 233, 1992; J. Am. Chem. Soc., Vol.116, page 10520, 1994).

Furthermore, the optically active reaction substrate and the asymmetric origin are generally difficult to obtain or prepare, and also they are expensive in most cases. Thus, it is strongly desired to develop any catalytically asymmetric synthetic reaction which can synthesize a plenty of an optically active compound from a small amount of an asymmetric origin.

In a field of organic synthetic chemistry, reactions with high yield and high selectivity are required, and recently synthetic reactions with decreased waste liquor and wastes are required additionally from viewpoints of circumstance problems etc., so that effective catalytical reactions are considered to contribute to decrease in quantity of experimental wastes.

From the said viewpoints, it is expected to realize a method with high yield and selectivity for an asymmetric imino aldol reaction as an asymmetric synthetic reaction of an optically active nitrogen-containing compound by using a catalyst, but there has not been hitherto known any catalytically asymmetric imino aldol reaction practically.

Thus, the invention of the present application has an object to overcome the conventional technical limitation and provide a novel asymmetric catalyst and a preparation thereof by which asymmetric organic syntheses such as an asymmetric imino aldol reaction etc. can be carried out with high reactivity and selectivity. Furthermore, the invention has an object to provide a preparation method of an optically active β-aminoester by using the above-mentioned asymmetric catalyst.

SUMMARY OF THE INVENTION

That is, the invention of the present application provides first an asymmetric zirconium catalyst having a constitution that zirconium (IV) in an active central atom of the catalyst and being bonded via oxygen atoms to two molecules of optically active binaphthyl groups (claim 1) in order to solve the above-mentioned problems.

And, there are provided as to the said catalyst the asymmetric zirconium catalyst wherein at least one hydrogen of an optically active binaphthyl group is substituted with halogen atom, nitro group, cyano group, alkyl group cycloalkyl group, aryl group or alkoxy group (claim 2); the asymmetric zirconium catalyst (claim 3) based on the structure expressed by the following formula (I) wherein an optically active binaphthyl group is 1,1'-bi-2-naphthyl group or 6,6'-dihalogeno-1,1'-bi-2-naphthyl group in either of R-form or S-form:

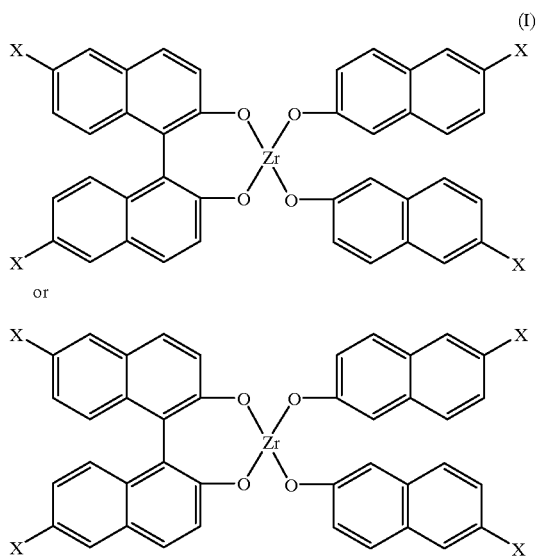

wherein, X=hydrogen or halogen atom;
the asymmetric zirconium catalyst wherein an optically active binaphtyl group is derived from the binaphtol expressed by the following formula (II) in either of R-form or S-form:

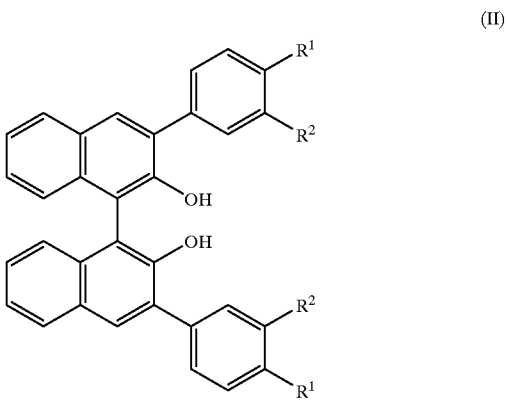

wherein, $R^1$, $R^2$=hydrogen or halogen atom, alkyl group, halogeno-alkyl group, nitro group, cyano group, or alkoxy group(claim 4); the asymmetric catalyst wherein an imidazole derivative or hydroxy-aromatic hydrocarbon derivative is coordinated to zirconium atom (claim 5); and an asymmetric catalyst wherein an imidazole derivative is at least one selected from the group of N-akylimidazoles and alkyl-substituted imidazoles (claim 6) as embodiments thereof.

Secondary, the invention of the present appilcation provides a method for forming the above-mentioned asymmetric zirconium catalyst (claim 7) characterized in that zirconium (IV) tetraalkoxide expressed by the following formula (III):

Zr(OR)4 (III)

wherein, R=alkyl group with 1 to 4 carbon atom, and the optically active binaphtol are reacted.

Furthermore., there are provided method for forming an asymmetric zirconium catalyst wherein zirconium (IV) tetraalkoxide is zirconium (IV) t-butoxide (claim 8) and the method for forming an asymmetric zirconium catalyst wherein zirconium (IV) t-butoxide and an optically active binaphthol are reacted in the presence of an imidazole derivative or hydroxy-aromatic hydrocarbon derivative (claim 9) as embodiments thereof.

In addition, thirdly, the invention of the present application provides a preparation method of an optically active compound by an addition reaction of imine or hydrazone and a nucleophile characterized in that they are reacted in the presence of the above-mentioned asymmetric zirconium catalyst (claim 10); as well as the method for forming an optically active compound wherein imine prepared from 2-aminophenol and a carbonyl compound is used as imine for an addition reaction with a nucleophile (claim 11); the method for forming an optically active compound wherein a nucleophile is silyl enol ether (claim 12); the method for forming an optically active compound by an addition reaction of imine or hydrazone and a nucleophile wherein they are reacted in the presence of the above-mentioned asymmetric zirconium catalyst with adding an imidazole derivative or hydroxy-aromatic hydrocarbon derivative into a reaction system as an additive (claim 13); and any of the above-mentioned preparation method wherein an optically active compound is β-aminoester (claim 14) as embodiments thereof.

DETAILED DESCRIPTION OF THE INVENTION

Figure 1:
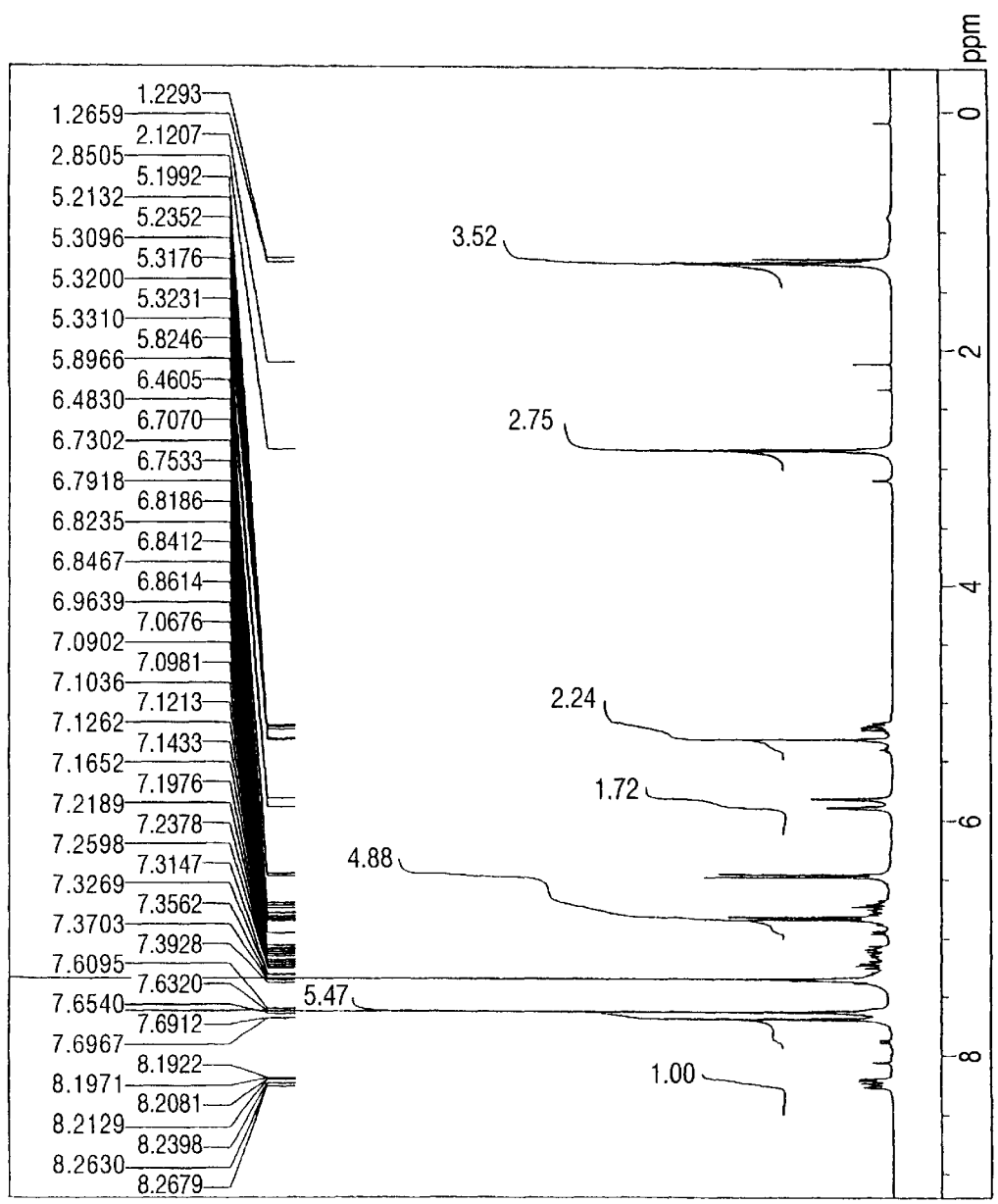
FIG. 1 shows a NMR spectral drawing of the catalyst obtained in Example 1.

Mode for carrying out the invention of the present application is illustrated as follows.

As described above, the asymmetric zirconium catalyst according to the invention has the following necessary conditions as to the essential basic structure:
1) zirconium (IV) being an active central atom of the catalyst, and
2) zirconium being bonded via oxygen atoms to two molecules of optically active binaphthyl groups. The optically active binaphthyl group in this case is derived from an optically active binaphthol wherein hydrogen (s) bonded to a ring in the naphthalene rings may be optionally substituted with various organic groups provided that the groups don't interfere functions of the asymmetric catalyst. For example, those in which at least one hydrogen being substituted with halogen atom, nitro group, cyano group, alkyl group, cycloalkyl group, aryl group or alkoxy group etc. are mentioned. Amongst of them, 1,1'-bi-2-naphthyl group and 6,6'-dihalogeno-1,1'-bi-2-naphthyl group in either of R-form or S-form expressed by the above-mentioned formula (I) are mentioned as preferable. 3,3'-aryl substituted-1,1'-bi-2-naphtlhyl group is either of R-from or S-form expressed by the above-mentioned formula (II) is also mentioned as prefereble.

In such asymmetric zirconium catalyst, an organic compound may be coordinated.

As the said organic compound, nitrogen-containing organic compounds may be preferably exemplified. Amongst, there are mentioned nitrogen-containing heterocyclic compounds such as imidazoles, indoles, pyrimidines and pyrazines etc. as well as diamine compounds. More concretely, N-alkyl imidazoles such as N-methyl imidazole and N-ethyl imidazole etc. as well as alkyl-substituted imidazoles such as 1,2-dimethy imidazole etc. are exemplified.

Organic compounds having at least of a hydroxy group also may be preferably used. Hydroxy-aromatichydrocarbons, such as hydroxy toluene, di-tert-butyl-hydroxytoluene, and hydroxyxylene are exemplified.

In use of the above-mentioned asymmetric zirconium catalyst, the asymmetric zirconium catalyst obtained by reacting zirconium (IV) tetraalkoxide typically expressed by the above-mentioned formula (III) and an optically active binaphthol may be used for any desired organic synthetic reaction with or without isolation from the synthetic system of the catalyst.

As to the synthetic system of the catalyst, any alkoxy group may be used in the case of zirconium (IV) tetraalkoxide being a raw material as described above, but lower alkoxy group, particularly t-butoxy group, may be exemplified as preferable.

Halogenated hydrocarbons, aromatichydrocarbons, amides and nitrites are used as reaction solvent, but it is preferably selected from solvents which do not interfere the said synthetic reaction and which are used also as solvent thereof in the case of catalyst being used for an organic synthetic reaction without isolation.

Temperature and time of catalytical synthetic reaction may be selected appropriately according to kinds of raw materials, and for example temperature may be generally at about −10 to 40° C.

The organic compound which can coordinate to above-mentioned imidazoles or hydroxy-aromatichydrocarbons may be added previously to a reaction system of a catalytic synthesis or may be added to an organic synthetic reaction system with use of a catalyst.

An introduced proportion of an optically active binaphthol to t-butoxide as zirconium (IV) raw material is basically about 2:1 in mole ratio. As to the organic compound such as imidazole, it may be about 1 to 3 times of molar amount of zirconium (V) raw material.

The above-mentioned asymmetric zirconium catalyst according to the invention can be used for various asymmetric organic synthetic reactions. Amongst, it is proposed to use the catalyst for preparation of an optically active compound by an addition reaction of imine or hydrozone and a nucleophile as the invention of the present application.

In the said reaction, imine may be an optional one such as obtained by a reaction of an amine compound and a carbonyl compound, and for example imine prepared from 2-aminophenole and a carbonyl compound may be mentioned which being useful as an organic synthetic intermediates as well as intermediates for medicines and pesticides.

On the other hand, the nucleophile may be any one and silyl enol other may be exemplified for an addition reaction with imine derived from 2-aminophenol.

Used amounts of the asymmetric zirconium catalysts in these organic synthetic reaction systems are different according to the reaction systems, but generally 0.1 to 50 mol %, more preferably 1 to 30 mol %. Reaction temperature and time are specified appropriately.

Examples of the present invention are illustrated as follows. Of course, the invention is not limited to these following examples.

EXAMPLE

Example 1

Tetra-t-butoxy zirconium (Zr(O-t-Bu)4, 4 mmol) was suspended in methylene chloride (25 ml), to which a solution of 6,6'-dibromo-1,1'-bi-2-naphthol (8 mmol) in methylene chloride (10 ml) and a solution of N-methyl imidazole (8 mmol) in methylene chloride (5 ml) were added and stirred for 1 hour. After distilling off the solvent under a reduced pressure and drying under a reduced pressure, an asymmetric zirconium catalyst (catalyst 1) having a structure shown by the above-mentioned formula (I) (X=Br) was obtained (yield; 4.56 g)

NMR spectra of the said catalyst 1 are shown in FIG. 1.

Then, the catalyst 1 (10 mol %) was dissolved in methylene chloride (0.25 ml) and cooled to −45° C. According to the following reaction formula, a solution of imine (0.8 mmol) prepared from 1-naphthaldehyde and 2-aminophenol in methylene chloride (0.5 ml) and then a solution of 1-methoxy-2-methyl-1-trimethylsiloxy propane (0.96 mmol) in methylene chloride (0.025 ml) were added and stirred for 10 hours, thereafter an aqueous saturated sodium hydrogencarbonate was added to stop the reaction. After extracting with methylene chloride and drying with anhydrous sodium sulfate, the solvent was distilled off under a reduced pressure. Tetrahydrofuran-1N hydrochloric acid were added to the obtained crude product and stirred for 30 minutes.

After distilling off the solvent under a reduced pressure, purification by means of silica gel column chromatography was carried out to obtain a compound quantitatively as a β-amino ester derivative. An optical purity (92%ee) of the obtained compound was determined.

Figure 2:
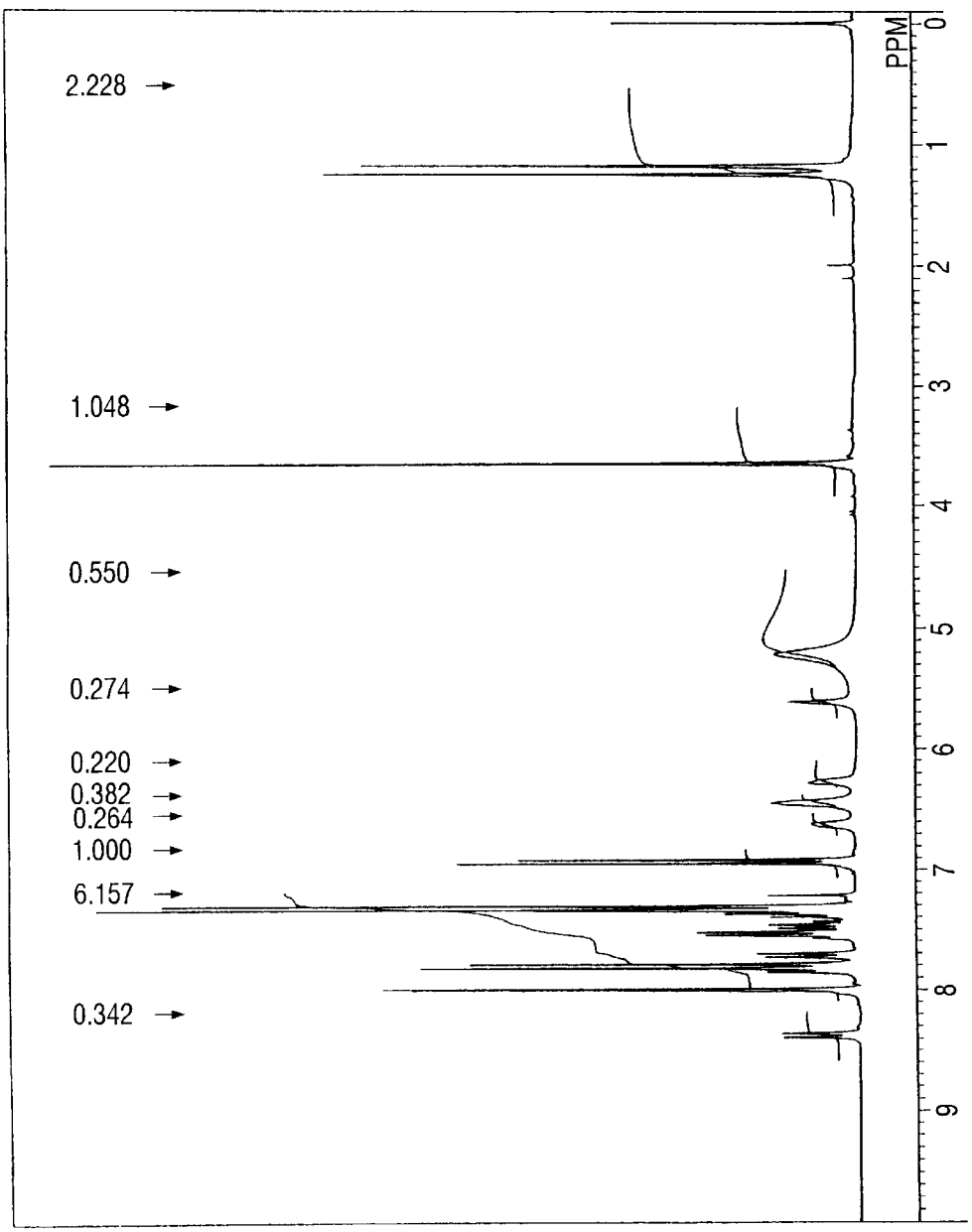
FIG. 2 shows a NMR spectral drawing of the product obtained in Example 1.
Figure 3:
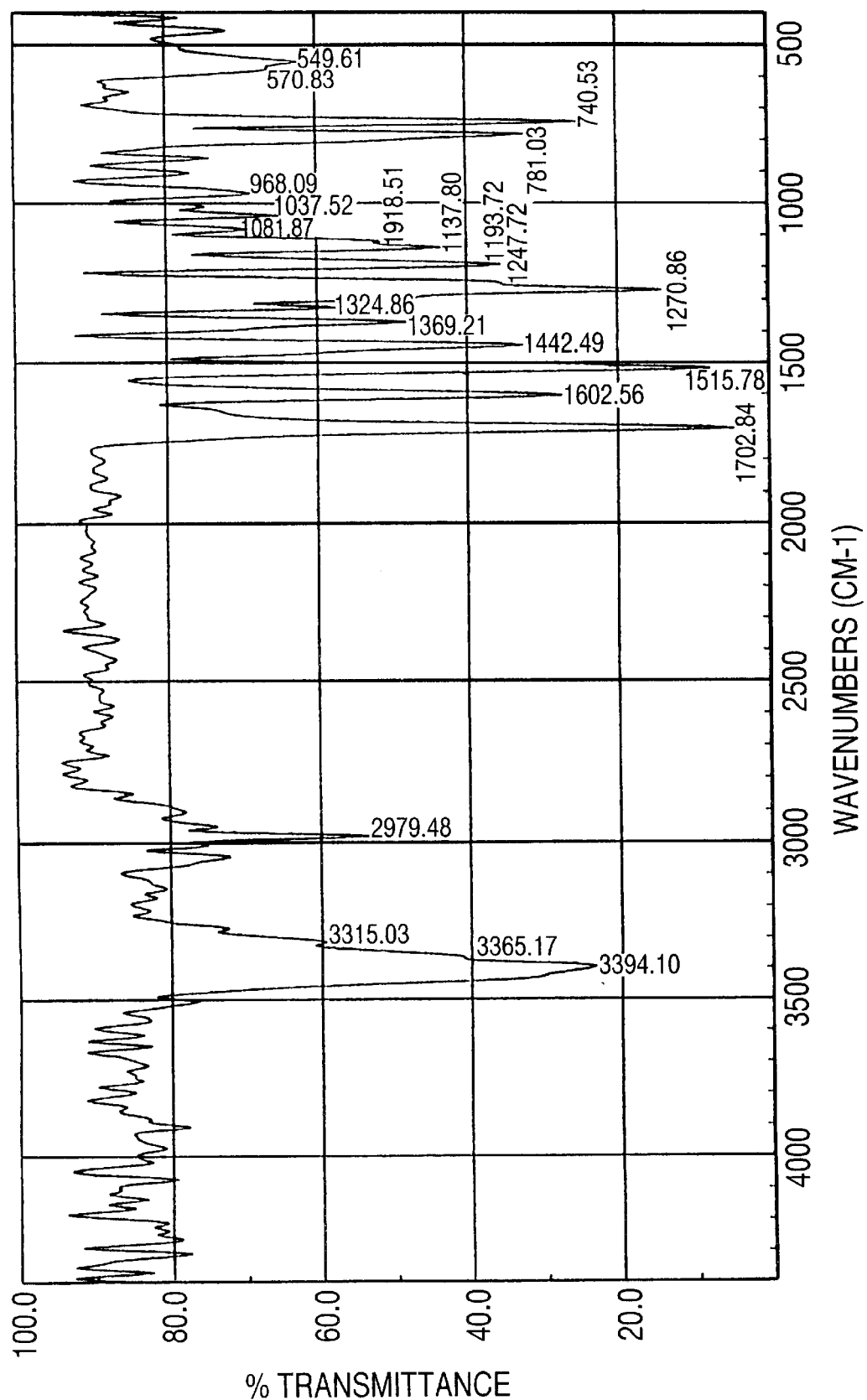
FIG. 3 shows a IR spectral drawing of the product obtained in Example 1.

NMR spectra of the compound are shown in FIG. 2 and IR spectra are shown in FIG. 3.

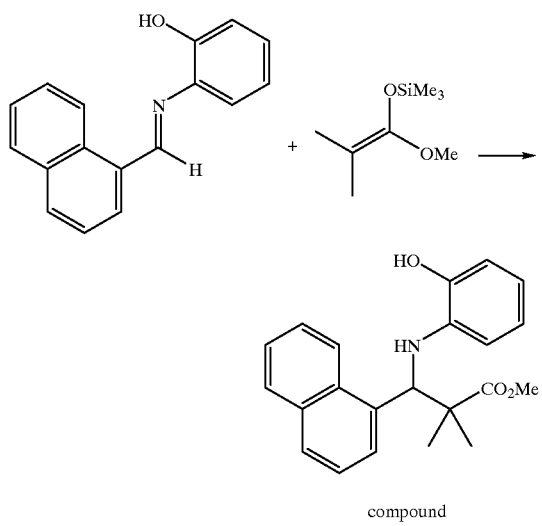

compound

Example 2

An asymmetric zirconium catalyst (catalyst 2) was obtained similarly to Example 1 by reacting 1,1'-bi-2-naphthol instead of 6,6'-dibromo-1,1'-bi-2-naphthol.

A synthetic reaction was carried out similar to Example 1 by using the said catalyst 2 to obtain the same compound with an yield of 80% and an optical purity of 70%ee.

Example 3

A catalyst (catalyst 3) was prepared similar to Example 1 except that N-methyl imidazole was not used and a synthetic reaction was carried out similar to Example 1 by using the said catalyst 3 to obtain the same compound with an optical purity of 54%ee.

Example 4

Tetra-t-butoxy zirconium (Zr(O-t-Bu)4, 0.04 mmol) was suspended in methylene chloride (0.25 ml), and then a solution of 6,6'-dibromo-1,1'-bi-2-naphthol (0.8 mmol) in methylene chloride (0.5 ml) and a solution of N-methyl imidazole (0.048 mmol) in methylene chloride (0.25 ml) were then added at the room temperature. After stirring for 1 hour and cooling to −45° C., a catalyst was prepared, and a synthetic reaction was carried out similar to Example 1 by using the said catalyst without isolation. The same compound was obtained quantitatively with an optical purity of 95%ee.

Example 5

A synthetic reaction was carried out similar to Example 4 by substituting N-methyl imidazole with 1,2-dimethyl imidazole at a temperature of −15° C. The same compound was obtained quantitatively with an optical purity of 91%ee.

Example 6

A synthetic reaction was carried out similar to Example 4 by changing an amount of a catalyst to ⅕ amount. The same compound was obtained with an yield of 75% and an optical purity of 86%ee.

Example 7

Reactions of various imines and silyl enolates were carried out according to the method similar to Example 4. Results are shown in Table 1.

TABLE 1

β-amino esters obtained (chemical yield/optical yield)

(70/87)

(quant/95)

TABLE 1-continued

β-amino esters obtained (chemical yield/optical yield)

(86/83)

(78/88)

(88/86)

(quant/96)

(89/89)

TABLE 1-continued

β-amino esters obtained (chemical yield/optical yield)

(45/80)

Reference Example

The compound obtained in Example 1 was subjected to a de-2-hydroxyphenylating reaction according to the following reaction formula. That is, the compound (0.4 mmol) was first dissolved in acetone (3 ml) and methyl iodide (1 ml) was added at the room temperature. After stirring for 8 hours, an aqueous saturated ammonium chloride solution was added with ice cooling to stop the reaction, extracted with methylene chloride, dried with anhydrous sodium sulfate, and thereafter distilled off the solvent to obtain a methyl ether compound. The said compound was dissolved in acetonitrile (3 ml) and an aqueous solution (1 ml) of ammonium cerium (IV) nitrate (1.2 mmol) was added with ice cooling. After 1 hour, the reaction solution was diluted with water and extracted with ethyl acetate. After the organic layer was washed subsequently with an aqueous solution of 5% sodium carbonate, an aqueous solution of 10% sodium bisulfate, an aqueous solution of 5% sodium carbonate and a saturated saline solution and dried with anhydrous sodium sulfate, the solvent was distilled off under a reduced pressure. Purification by means of silica gel column chromatography was carried out to obtain a β-amino ester derivative (yield 67).

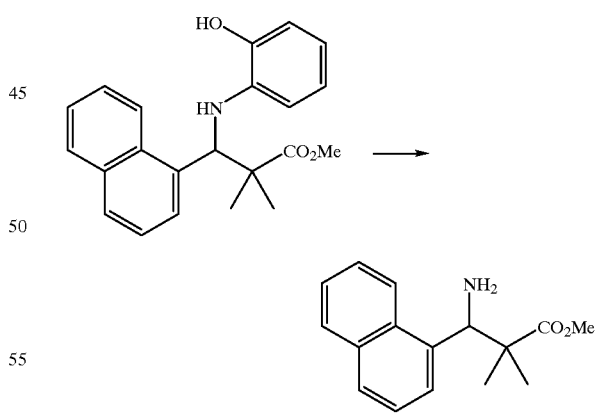

Example 8

A chiral catalyst was prepared similar to Example 1 except that N-methyl imidazole was not used.

Then, the chiral catalyst (20 mol %) was used with 3,5-di-tert-butyl-4-hydroxytoluene (BHT) for a reaction between N-benzoylhydrozone (1) and ketenesilylacetal (2) is toluene according to the following reaction formula.

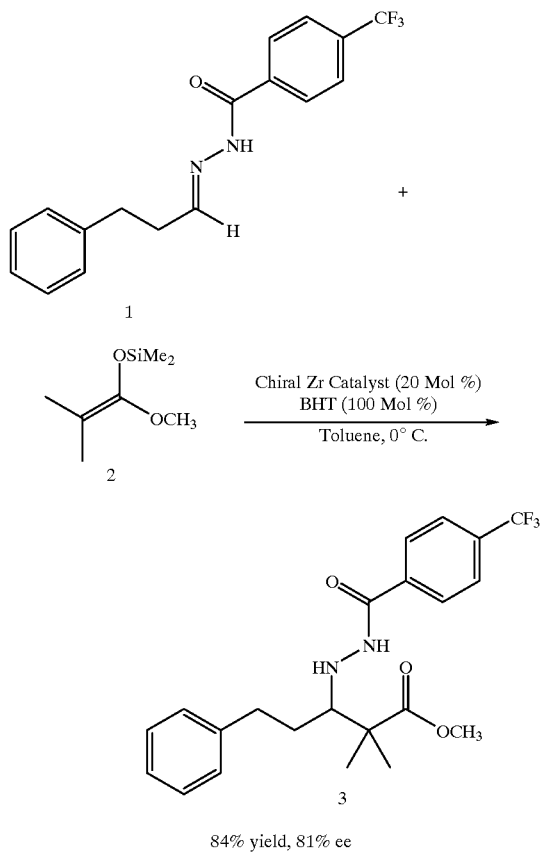

84% yield, 81% ee

After the reaction, β-hydrazinoester (3) was obtained with high yield (84%) and high stereo selectivity (81% ee).

A β-amino ester derivative was obtained from the β-hydrazinoester (3) by reductively cutting reaction of the N—N bond.

Example 9

Catalysts were prepared from $Zr(O^tBu)_4$ and several kinds of binaphtol (BINOL 1~3) expressed by the following formula,

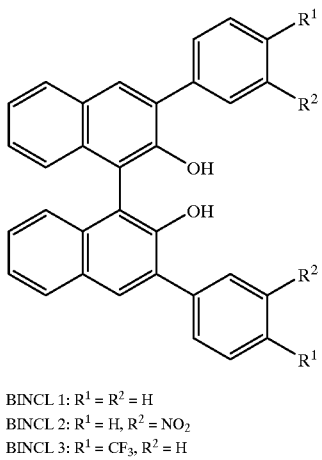

BINCL 1: $R^1 = R^2 = H$
BINCL 2: $R^1 = H, R^2 = NO_2$
BINCL 3: $R^1 = CF_3, R^2 = H$

Aza Diels-Alder reaction between imine and Danishefsky's diene was carried out by using the above mentioned catalysts.

In detailed, for example, a chiral zirconium catalyst was prepared by using $Zr(O^tBu)_4$ (10 mol %), (R)-BINOL 1~3 (20 mol %) and N-methyl imidazole (30 mol %).

Said the chiral catalysts were used for the aza Diels-Alder reaction above-mentioned.

According to the following reaction formula, imines were reacted with Danishefsky's diene in toluene at the temperature of −45° C. in the presence of said the chiral catalyst.

Corresponding piperidine derivatives ((S)-form) were obtained with high yield and high optical purity.

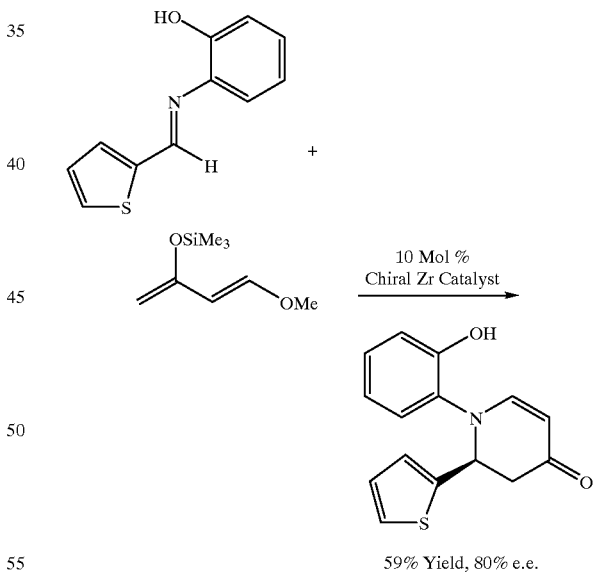

59% Yield, 80% e.e.

The invention of the present application provides an optically active β-amino ester with high chemical yield and high asymmetric yield by proceeding an imino aldol reaction catalytically by means of a novel asymmetric catalyst, as described above in detail. Furthermore, the catalyst is useful as an asymmetric catalyst not only for an imino aldol reaction but also for similar reactions.

What is claimed is:

1. An asymmetric zirconium catalyst having a constitution that zirconium (IV) is an active central atom of the catalyst and being bonded via oxygen atoms to two molecules of optically active binaphthyl groups.

2. The asymmetric zirconium catalyst according to claim 1, wherein at least one hydrogen of an optically active binaphthyl group is substituted with halogen atom, nitro group, cyano group, alkyl group, cycloalkyl group, aryl group or alkoxy group.

3. The asymmetric zirconium catalyst according to claim 1 based on the structure expressed by the following formula (I), wherein the optically active binaphthyl group is 1,1'-bi-2-naphthyl group or 6,6'-dihalogeno-1,1'-bi-2-naphthyl group in either of R-form or S-form:

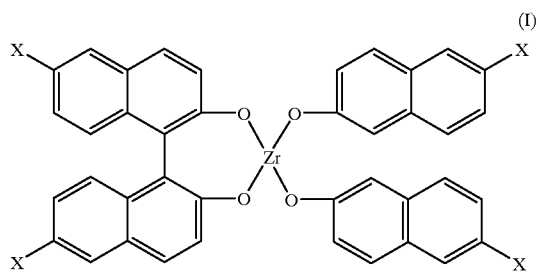

wherein, X=hydrogen or halogen atom.

4. A The asymmetric zirconium catalyst according to claim 1 or 2, wherein the optically active binaphtyl group is derived from the binaphthol expressed by the following formula (II) in either of R-form or S-form:

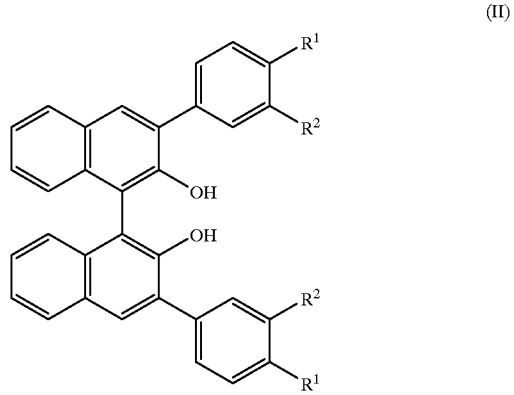

wherein, $R^1$, $R^2$=hydrogen or halogen atom, alkyl group, halogeno-alkyl group, nitro group, cyano group, or alkoxy group.

5. The asymmetric catalyst, wherein an imidazole or hydroxy-aromatic hydrocarbon derivative is coordinated to zirconium atom of an asymmetric zirconium catalyst according to any of claims 1 to 3.

6. The asymmetric catalyst according to claim 5, wherein a imidazole derivative is at least one selected from the group consisting of N-alkylimidazoles and alkyl-substituted imidazoles.

7. A method for forming an asymmetric zirconium catalyst according to any of claims 1 to 3, wherein zirconium (IV) tetraalkoxide expressed by the following formula (III):

Zr(OR)4   (III)

wherein, R=alkyl group with 1 to 4 carbon atom, and the optically active binaphthol are reacted.

8. The method for forming an asymmetric zirconium catalyst according to claim 7, wherein zirconium (IV) tetraalkoxide is zirconium (IV) t-butoxide.

9. The method for forming an asymmetric zirconium catalyst according to claim 8, wherein zirconium (IV) t-butoxide and an optically active binaphthol are reacted in the presence of an imidazole derivative or hydroxy-aromatic hydrocarbon derivative.

10. The method for forming an optically active compound by an addition reaction of imine or hydrazone and a nucleophile characterized in that they are reacted in the presence of an asymmetric zirconium catalyst according to any of claims 1 to 3.

11. The method for forming an optically active compound according to claim 10, wherein imine prepared from 2-aminophenol and a carbonyl compound is used as imine for an addition reaction with a nucleophile.

12. The method for forming an optically active compound according to claim 10, wherein a nucleophile is silyl enol ether.

13. The method for forming an optically active compound by an addition reaction of imine or hydrazone and a nucleophile characterized in that they are reacted in the presence of an asymmetric zirconium catalyst according to any of claims 1 to 3 with adding an imidazole derivative or hydroxy-aromatic hydrocarbon derivative into a reaction system as an additive.

14. The method for forming an optically active compound according to claim 10 to, wherein an optically active compound is β-aminoester, β-hydrazinoester or piperidine derivative.

15. The asymmetric zirconium catalyst according to claim 3, where X=hydrogen.

* * * * *